US012782313B2

(12) United States Patent
Akasaka et al.

(10) Patent No.: US 12,782,313 B2
(45) Date of Patent: Nov. 3, 2026

(54) SENSOR SYSTEM

(71) Applicant: Rohm Co., Ltd., Kyoto (JP)

(72) Inventors: Shunsuke Akasaka, Kyoto (JP); Ken Nakahara, Kyoto (JP); Takashi Naiki, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 137 days.

(21) Appl. No.: 18/815,401

(22) Filed: Aug. 26, 2024

(65) Prior Publication Data

US 2024/0418670 A1 Dec. 19, 2024

Related U.S. Application Data

(63) Continuation of application No. PCT/JP2023/007060, filed on Feb. 27, 2023.

(30) Foreign Application Priority Data

Mar. 2, 2022 (JP) ................................ 2022-031708

(51) Int. Cl.

| | |
|---|---|
| ***G01N 27/407*** | (2006.01) |
| ***G01N 27/327*** | (2006.01) |
| ***G01N 27/416*** | (2006.01) |
| *G01N 33/00* | (2006.01) |

(52) U.S. Cl.

CPC ....... *G01N 27/407* (2013.01); *G01N 27/3274* (2013.01); *G01N 27/4163* (2013.01); *G01N 33/0031* (2013.01)

(58) Field of Classification Search

CPC ............. G01N 27/407; G01N 27/4163; G01N 27/327–3274; G01N 33/0031; G01N 33/4836; A61B 5/082; A61B 5/083; A61B 5/0833

See application file for complete search history.

(56) References Cited

U.S. PATENT DOCUMENTS 5,769,063 A * 6/1998 Mizusawa ........... F02D 41/1495 123/688
2005/0155405 A1* 7/2005 Sasaki ............... H01M 8/04089 73/1.06
2006/0042960 A1* 3/2006 Tice ................... G01N 33/0006 204/406

FOREIGN PATENT DOCUMENTS

| | | | |
|---|---|---|---|
| DE | 4305934 A1 * | 9/1994 | ............ G01N 25/56 |
| JP | 5-209860 | 8/1993 | |
| JP | 6-273372 | 9/1994 | |
| JP | 2000-121601 | 4/2000 | |
| JP | 2010-519514 | 6/2010 | |
| JP | 2014-182098 | 9/2014 | |
| JP | 2017-531161 | 10/2017 | |
| JP | 2019-085284 | 6/2019 | |

(Continued)

OTHER PUBLICATIONS

EPO machine-generated English language translation of DE 4305934 A1, patent published Sep. 1, 1994 (Year: 1994).*
International Search Report issued in International Application No. PCT/JP2023/007060, May 9, 2023, 7 pages with translation.

(Continued)

*Primary Examiner* — Alexander S Noguerola
(74) *Attorney, Agent, or Firm* — HSML P.C.

(57) ABSTRACT

A plurality of yttria-stabilized zirconia sensors, a drive device, and a controller are provided. The drive device drives each of the plurality of sensors. The controller the controller sequentially switches between/among the plurality of sensors based on a prescribed condition.

16 Claims, 10 Drawing Sheets

(56) References Cited

FOREIGN PATENT DOCUMENTS

| | | |
|---|---|---|
| JP | 2021-124473 | 8/2021 |
| WO | 2017/014033 | 1/2017 |

OTHER PUBLICATIONS

Written Opinion issued in International Application No. PCT/JP2023/007060, May 9, 2023, 9 pages with translation.

* cited by examiner

SENSOR SYSTEM

TECHNICAL FIELD

The present disclosure relates to a sensor system.

BACKGROUND ART

For example, a sensor such as a galvanic cell oxygen sensor, a polymer humidity sensor, or a bulk yttria-stabilized zirconia sensor has been known as a sensor that detects an oxygen concentration and/or a humidity. Japanese Patent Laying-Open No. 2021-124473 (PTL 1) discloses a limiting-current type oxygen sensor that can detect an oxygen concentration and a water vapor concentration. Incorporating these sensors, a sensor system that requires a value of the oxygen concentration and/or a value of the humidity can obtain information on the oxygen concentration and/or the humidity based on detection values from the sensors.

CITATION LIST

Patent Literature

PTL 1: Japanese Patent Laying-Open No. 2021-124473

DESCRIPTION OF EMBODIMENTS

Figure 1:
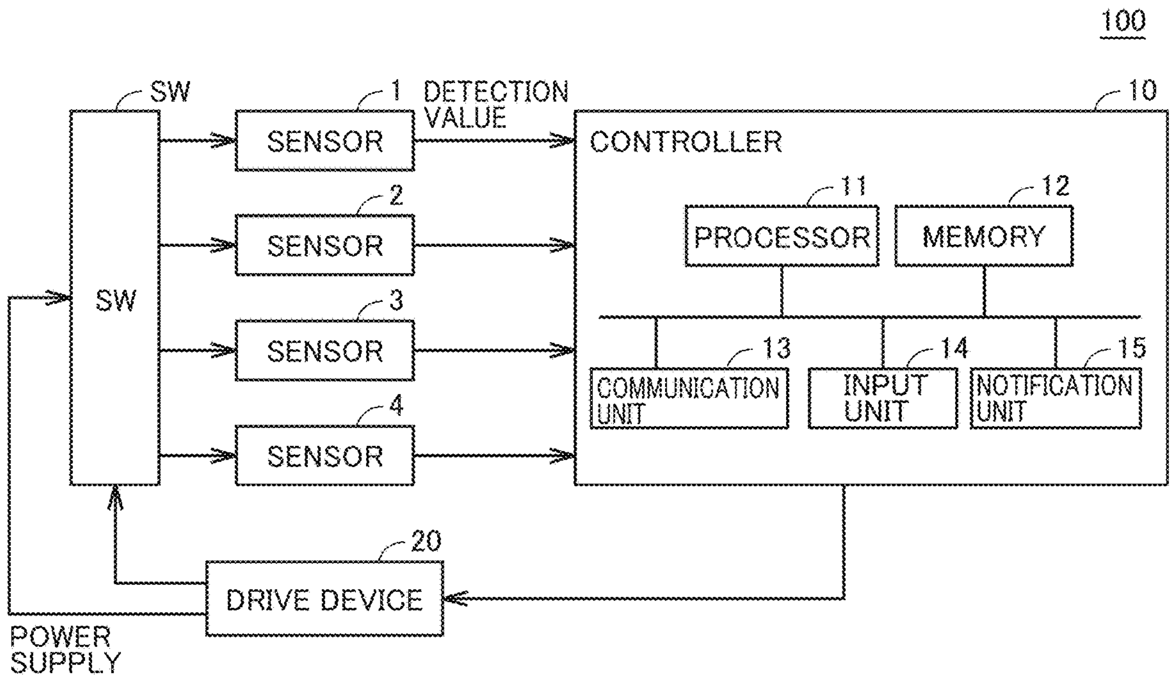
FIG. 1 is a schematic diagram showing a configuration of a sensor system according to an embodiment.

An embodiment of the present invention will be described in detail below with reference to the drawings. The same or corresponding elements in the drawings have the same reference characters allotted and description thereof will not be repeated.

1. Configuration of Sensor System

FIG. 1 is a schematic diagram showing a configuration of a sensor system 100 according to an embodiment of the present invention. Referring to FIG. 1, sensor system 100 includes sensors 1 to 4, a controller 10, a drive device 20, and a switch SW. Sensors 1 to 4 are YSZ sensors. When a prescribed voltage is applied to sensors 1 to 4 in a high-temperature state, sensors 1 to 4 generate limiting currents corresponding to a concentration of gas introduced in sensors 1 to 4. The concentration of gas herein refers to an oxygen concentration and/or a water vapor concentration (humidity) unless otherwise specified. The limiting current is detected by a current detector (not shown) included in each of sensors 1 to 4, and a value of the measured current is converted to the concentration of gas by a gas concentration calculator (not shown) included in each of sensors 1 to 4. The detected concentration of gas (which is also referred to as a "detection value" below) is transmitted to controller 10. Since a more specific configuration and principles of the YSZ sensor are described in detail in PTL 1, description will not be given here. Sensors 1 to 4 correspond to one example of the "plurality of sensors."

Sensors 1 to 4 are, for example, YSZ sensors of a small size having a maximum dimension not larger than approximately 5 mm. More specifically, sensors 1 to 4 are the YSZ sensors of a small size having the maximum dimension not larger than approximately 1 mm. By employing such YSZ sensors of the small size, even when a plurality of sensors are incorporated, the entire sensor system 100 can also be small in size. Sensor system 100 of the small size is thus suitable for incorporation in a portable device, and it is relatively easily provided in a narrow space in the inside of a device and a narrow space such as a small room (see [4. Application]).

Switch SW makes switching among sensors 1 to 4 based on a command from controller 10.

Drive device 20 has electric power supplied to sensors 1 to 4 with switch SW being interposed. Drive device 20 controls switch SW to make switching among sensors 1 to 4 to be used based on the command from controller 10. The drive device thus drives each of sensors 1 to 4.

The controller controls switch SW and drive device 20 based on a prescribed condition to sequentially make switching among sensors 1 to 4. Controller 10 includes a processor 11, a memory 12, a communication unit 13, an input unit 14, and a notification unit 15 connected to one another through a common bus.

Processor 11 includes, for example, a central processing unit (CPU). Processor 11 develops a program stored in memory 12 on a RAM or the like and executes the same.

Memory 12 is implemented by a non-volatile memory such as a random access memory (RAM), a read only memory (ROM), and a flash memory. A program to be executed by processor 11 or data to be used by processor 11 is stored in memory 12.

Communication unit 13 is a communication interface for communication of various types of data between controller 10, and sensors 1 to 4 and drive device 20. Communication may be communication through a wire or wireless communication. Input unit 14 receives an operation input for sensor system 100 from a user. Input unit 14 includes, for example, a keyboard, a mouse, and the like. Notification unit 15 includes a liquid crystal display, a speaker, and/or the like.

In each of sensors 1 to 4 herein, drive and use thereof are assumed as being in coordination. More specifically, while sensors 1 to 4 are driven, detection values from sensors 1 to 4 are transmitted to controller 10 and processed in controller 10. When supply of electric power to sensors 1 to 4 is stopped, sensors 1 to 4 are also deactivated and detection values from sensors 1 to 4 are not processed in controller 10. In other words, use of sensors 1 to 4 and drive of sensors 1 to 4 herein correspond to each other.

2. Comparison with Conventional Sensor System

In a sensor system required to detect an oxygen concentration and/or a water vapor concentration, a galvanic cell oxygen sensor, a polymer humidity sensor, or a bulk YSZ sensor has been used. In the sensor system, for example, the oxygen concentration and/or the water vapor concentration are/is detected based on a detection value from the sensor, and whether the detected concentration is in a normal range or abnormal is detected. More specifically, whether a state of a device or an environment where the sensor system is provided is normal or abnormal can be determined based on the detected concentration. Therefore, it is important for the sensor to output an appropriate detection value in accordance with the concentration of gas in such a sensor system.

It has been known, however, that such a sensor may give an inappropriate detection value when the sensor deteriorates. Therefore, a user of the sensor system should pay attention to failure due to deterioration. The galvanic cell oxygen sensor or the polymer humidity sensor has been known to start to irreversibly deteriorate from a time point when a wrapper of the sensor is opened. The bulk YSZ sensor has been known to irreversibly deteriorate in a high-temperature state although it should be in the high-temperature state for measurement of a gas concentration. Therefore, when such a sensor fails due to deterioration, the sensor should be replaced or the sensor system itself should be replaced. At that time, the user should suspend use of the sensor system, which has been inconvenient for the user who needs monitoring of the gas concentration by the sensor system. Specifically, continued monitoring of the concentration of gas by the sensor system cannot be performed, which necessitates cost and man-hours for maintenance.

Sensor system 100 according to the present embodiment includes a plurality of YSZ sensors, and the controller sequentially makes switching between/among the plurality of sensors based on a prescribed condition. Thus, even when one sensor fails due to deterioration or the like, switching to another sensor is automatically made and measurement is continued. Therefore, in the sensor system including sensors that deteriorate over time as they are used, a period for which the sensor system is kept operable without maintenance by the user can be longer.

Present sensor system 100 includes a YSZ sensor different in characteristics from a general galvanic cell sensor and a general polymer humidity sensor. For example, the YSZ sensor is higher in heat resistance than the general galvanic cell sensor. Therefore, present sensor system 100 is applicable even to an example to which application of the galvanic cell sensor or the polymer humidity sensor is difficult. In particular, by employing the YSZ sensor of the small size, present sensor system 100 is applicable even to an example in which incorporation of the bulk YSZ sensor (having the maximum dimension of approximately 2 to 3 cm) is difficult due to its size or incorporation of a plurality of sensors is difficult.

3. Flow of Processing by Sensor System

Figure 2:
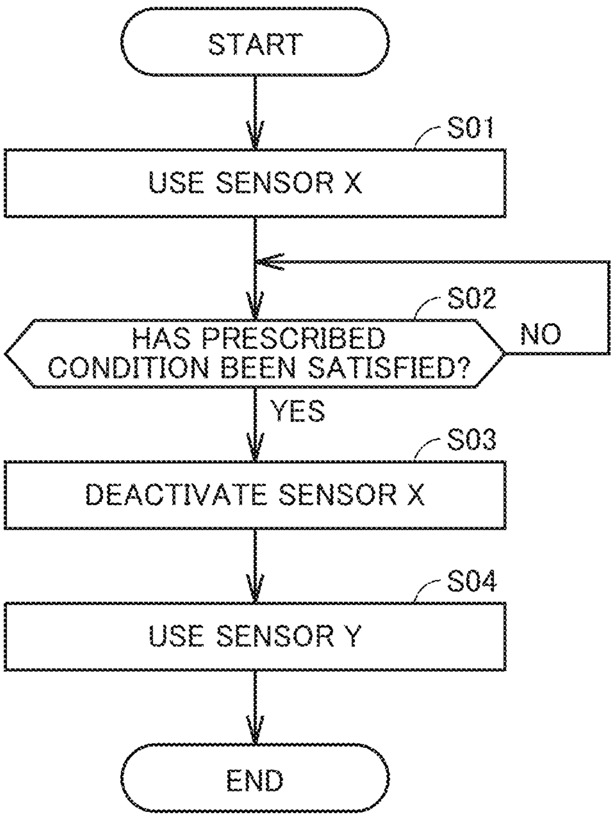
FIG. 2 is a flowchart showing control processing in the sensor system according to the embodiment.

Control processing by sensor system 100 will now be described. FIG. 2 is a flowchart showing control processing in sensor system 100 according to the embodiment. Processing in FIG. 2 is performed by sensor system 100 including controller 10.

In step (which will also simply be referred to as "S" below) 01, controller 10 causes use of a sensor X which is at least one of a plurality of sensors included in sensor system 100.

In S02, controller 10 determines whether or not a prescribed condition is satisfied. When the prescribed condition is not satisfied (NO in S02), controller 10 has the process return to S02.

When sensor X satisfies the prescribed condition (YES in S02), in S03, controller 10 deactivates sensor X. In succession, in S04, controller 10 causes use of a sensor Y which is at least one sensor different from sensor X among the plurality of sensors included in sensor system 100.

As set forth above, sensor system 100 according to the present embodiment can sequentially make switching between/among the plurality of sensors based on the prescribed condition. Thus, even when one sensor becomes inoperable, switching to another sensor is automatically made and measurement is continued, and hence use of sensor system 100 can be continued.

Various types of control in sensor system 100 according to the present embodiment will be described below.

3-1. First Embodiment

In a first embodiment, control for switching among the sensors based on lifetime of the sensors will be described.

Figure 3:
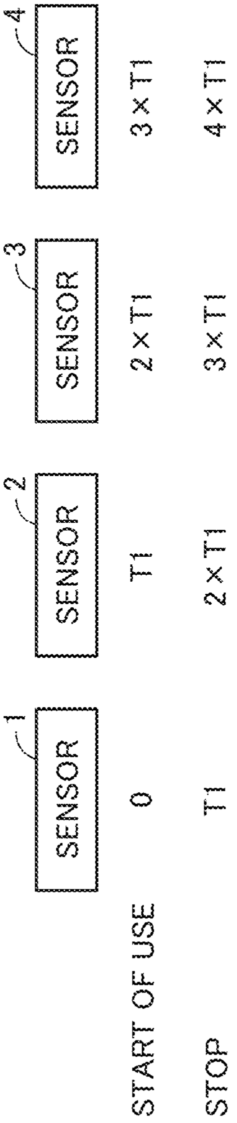
FIG. 3 is a schematic diagram for illustrating control in the sensor system according to a first embodiment.

FIG. 3 is a schematic diagram for illustrating control in sensor system 100 according to the first embodiment. FIG. 3 shows time of start and stop of use of sensors 1 to 4.

Use of sensor 1 is started with start of use of sensor system 100, and when a first period T1 elapses, switching to sensor 2 is made. First period T1 refers to a period after which a degree of deterioration of the sensor due to use exceeds a certain defined value. The "degree of deterioration due to use exceeding the certain defined value" is herein also referred to as "failure due to deterioration." "First period T1" is also referred to as "lifetime of the sensor." First period T1 is more specifically a period until a detection value from the sensor, of gas at a prescribed concentration becomes equal to or smaller than a prescribed threshold value. The prescribed threshold value is, for example, a value as large as 90 to 95% of the detection value from a sensor that has not deteriorated. First period T1 is, for example, 3000 hours.

In other words, in sensor system 100 according to the first embodiment, the prescribed condition is a "condition that a total period of use of each of the plurality of sensors exceeds the first period" and switching among the sensors is made in accordance with the condition. The condition above corresponds to one example of the "first condition" in the present disclosure.

When sensor 2 or another sensor that follows is used for first period T1, switching to the next sensor is also similarly made.

Figure 4:
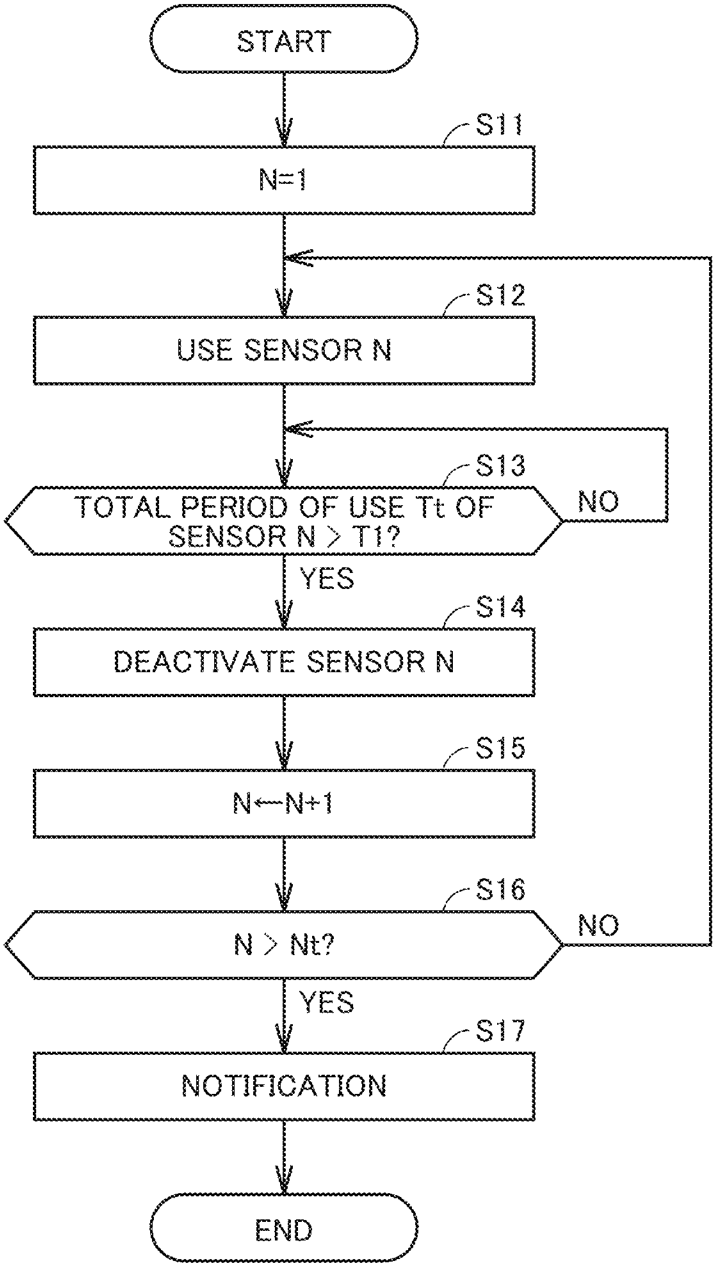
FIG. 4 is a flowchart showing control processing in the sensor system according to the first embodiment.

FIG. 4 is a flowchart showing control processing in the sensor system according to the first embodiment. Processing in FIG. 4 is performed by sensor system 100 including controller 10.

In S11, controller 10 substitutes 1 into a counter N.

In S12, controller 10 causes use of a sensor N.

In S13, controller 10 determines whether or not a total period of use Tt of sensor N exceeds first period T1. Total period of use Tt is measured, for example, by controller 10. When total period of use Tt is equal to or shorter than first period T1 (NO in S13), controller 10 has the process return to S13.

When total period of use Tt exceeds T1 (YES in S13), in S14, controller 10 deactivates sensor N.

In S15, controller 10 increments a value of counter N by one.

In S16, controller 10 determines whether or not the value of counter N is larger than a defined value Nt. Defined value Nt represents the number of sensors incorporated in sensor system 100, and in the example in FIG. 3, the number is set to four. In other words, the value of counter N being larger than defined value Nt (YES in S16) indicates that all sensors have already been used.

When the value of counter N is larger than defined value Nt (YES in S16), controller 10 quits the process relating to switching among the sensors. Before quitting the process, however, in S17, controller 10 may cause notification unit 15 to give notification that total periods of use Tt of all sensors have exceeded first period T1. Controller 10 can thus remind the user of replacement of the sensor in sensor system 100 or replacement of sensor system 100 itself. Consequently, the user can determine next measures such as replacement or monitoring of the detection value from the sensor by the user himself/herself.

When the value of counter N is equal to or smaller than defined value Nt (NO in S16), on the other hand, there is an unused sensor in sensor system 100 and controller 10 has the process return to $12.

Since processing during a period from deactivation of the previous sensor based on the prescribed condition until use of the next sensor (S15 to S16) is computation in a computer, it is performed in an extremely short time period (for example, within one second). In other words, since switching among the sensors is made in an extremely short time period, interruption of measurement due to switching also lasts for an extremely short time period, which virtually does not give rise to a problem. If there is still a problematic situation, however, the configuration may be such that the previous sensor is not immediately deactivated even when the prescribed condition is satisfied, and the previous sensor is deactivated simultaneously with or immediately after the next sensor is determined and use thereof is started. Similarly in subsequent second to fourth embodiments, processing from deactivation of the previous sensor based on the prescribed condition until use of the next sensor takes an extremely short time period, which does not give rise to a problem in monitoring of the concentration of gas. The configuration, however, may be such that the previous sensor is deactivated simultaneously with start of use of the next sensor.

As set forth above, in control processing in sensor system 100 according to the first embodiment, when total period of use Tt of a specific sensor (corresponding to one example of the "first sensor") in sensor system 100 exceeds first period T1 while the specific sensor is being used, controller 10 makes switching from the specific sensor to another sensor (corresponding to one example of the "second sensor"). Therefore, since switching to the next sensor can be made before lifetime of the specific sensor comes, sensor system 100 does not have to be shut down for maintenance when lifetime of the specific sensor comes. Therefore, a period for which the sensor system including the sensor that deteriorates as it is used can be used without maintenance of the sensor can be longer in the sensor system.

3-2. Second Embodiment

Figure 5:
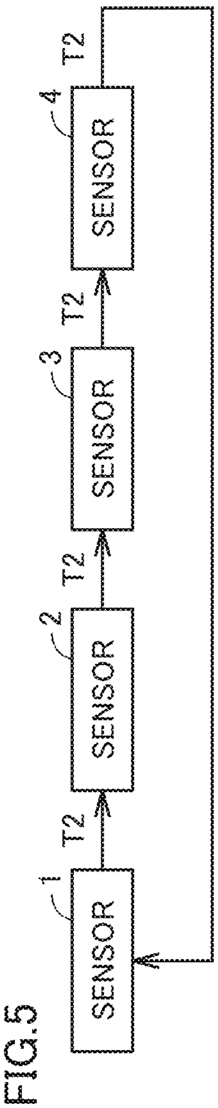
FIG. 5 is a schematic diagram for illustrating control in the sensor system according to a second embodiment.

In a second embodiment, such control that sensors 1 to 4 are used by rotation will now be described. FIG. 5 is a schematic diagram for illustrating control in sensor system 100 according to the second embodiment. Referring to FIG. 5, when each of sensors 1 to 4 is used for a second period T2 shorter than first period T1, switching to the next sensor is made. Second period T2 is set, for example, to one hour. In other words, in sensor system 100 according to the second embodiment, the prescribed condition is a condition that "a period of continuous use of each of the plurality of sensors exceeds the second period" and switching among the sensors is made in accordance with the condition. The condition above corresponds to one example of the "second condition" in the present disclosure.

Simply with the configuration above, a sensor a detection value from which is inappropriate due to sudden failure is also repeatedly used by rotation. In order to solve this problem, when the detection value from the sensor is inappropriate, desirably, use of the sensor is prohibited and the sensor is not included in rotation from this point onward. In a following flowchart, rotation control including also processing for prohibiting use of such a sensor will be described.

Figure 6:
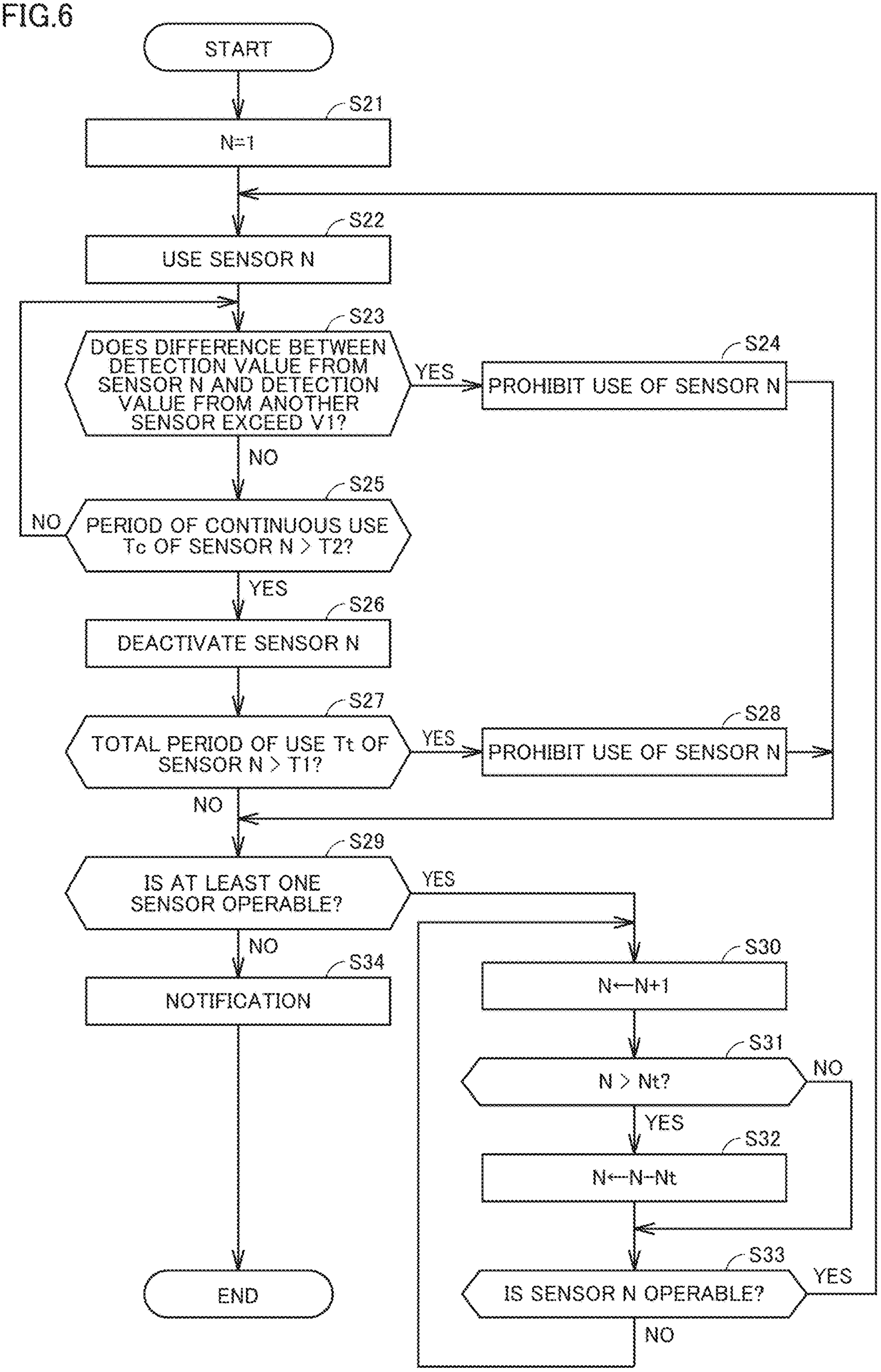
FIG. 6 is a flowchart showing control processing in the sensor system according to the second embodiment.

FIG. 6 is a flowchart showing control processing in sensor system 100 according to the second embodiment. Processing in FIG. 6 is performed by sensor system 100 including controller 10.

In S21, controller 10 substitutes 1 into counter N.

In S22, controller 10 causes use of sensor N.

In S23, controller 10 determines whether or not a difference between a detection value from sensor N being used and a detection value from at least one other sensor exceeds a first threshold value V1. First threshold value V1 is a threshold value for determination as to failure due to deterioration of the sensor, and it is a value indicating the difference between the detection value when failure due to deterioration occurs and the detection value from another sensor that has not deteriorated. In the example in FIG. 6, first threshold value V1 is set, for example, to a value as large as 5 to 10% of the detection value from another sensor. For comparison in detection value between the sensors, for example, an average value of the detection values for a prescribed period is used. The prescribed period is set, for example, to one minute.

In the process in FIG. 6, when S23 is performed for the first time, there is no detection value from another sensor, and a predetermined alternative value is inputted as the detection value from another sensor. The alternative value is determined in advance, for example, based on specifications of the sensor or an expected environment of use of sensor system 100.

When the difference between the detection value from sensor N and another detection value exceeds first threshold value V1 (YES in S23), in S24, controller 10 prohibits use of sensor N. In other words, in sensor system 100, sensor N is not used from this point onward.

When the difference between the detection value from sensor N and another detection value is equal to or smaller than first threshold value V1 (NO in S23), in S25, controller 10 determines whether or not a period of continuous use Tc of sensor N exceeds second period T2. Period of continuous use Tc is measured, for example, by controller 10.

When period of continuous use Tc of sensor N is equal to or shorter than second period T2 (NO in S25), controller 10 has the process return to S23.

When period of continuous use Tc of sensor N exceeds second period T2 (YES in S25), in S26, controller 10 deactivates sensor N.

In S27, controller 10 determines whether or not total period of use Tt of sensor N exceeds first period T1. When total period of use Tt exceeds first period T1 (YES in S27), in S28, controller 10 prohibits use of sensor N.

When total period of use Tt is equal to or shorter than first period T1 (NO in S27), in S29, controller 10 determines whether or not at least one sensor is operable in sensor system 100. The sensor being inoperable is typically due to prohibition of use of the sensor. Without being limited as such, the sensor being inoperable may include a state where the sensor is inoperable due to other factors such as sudden failure of the sensor, the switch, or the like or defective connection.

When all sensors are inoperable (NO in S29), controller 10 quits the process relating to switching among the sensors. Before quitting the process, however, in S34, controller 10 may have notification unit 15 to give notification that all sensors have been determined as being inoperable. Controller 10 can thus remind the user of replacement of the sensor in sensor system 100 or replacement of sensor system 100 itself. In addition, the configuration may be such that while notification about break is given each time each sensor breaks, use of sensor system 100 is continued. The user can thus estimate timing of inoperability of all sensors and prepare for maintenance.

In S30 to S33, controller 10 determines whether or not the next sensor is operable. Specifically, in S30, controller 10 increments the value of counter N by one. The controller determines whether or not the value of counter N is larger than defined value Nt. As set forth above, defined value Nt represents the number of sensors incorporated in sensor system 100, and in the example in FIG. 5, the number is set to four.

When the value of counter N is larger than defined value Nt (YES in S31), in S32, controller 10 substitutes (N−Nt) into counter N. In the example in FIG. 5, when N is set to N=5, in S32, N−Nt=5−4=1 is substituted into N.

When the value of counter N is equal to or smaller than defined value Nt (NO in S31) or subsequent to S32, in S33, controller 10 determines whether or not sensor N is operable.

When new sensor N is inoperable (NO in S33), controller 10 has the process return to S30 and determines whether or not the second next sensor is operable.

When new sensor N is operable (YES in S33), controller 10 has the process return to S22 and use of sensor system 100 is continued with sensor N being used.

Processing including S23 to S24 where the sensor that has deteriorated is determined based on the detection value from each sensor and use thereof is prohibited is not limited to the example above. The processing may be, for example, processing for comparing detection values from all sensors with one another and prohibiting use of a sensor a detection value from which is an outlier based on majority rule. The detection value being an outlier refers, for example, to a difference in detection value from another sensor exceeding first threshold value V1.

As set forth above, in control processing in sensor system 100 according to the second embodiment, controller 10 controls the plurality of sensors to be used by rotation each for second period T2 shorter than first period T1. In addition, when the difference between the detection value from the sensor being used and the detection value from at least one other sensor exceeds first threshold value V1, controller 10 prohibits use of the sensor being used and makes switching to another sensor.

By thus using the plurality of sensors as in the first embodiment, a period for which the sensor system can be used without maintenance of the sensor can be longer. When the detection value from the sensor is inappropriate, use of the sensor that gives the inappropriate detection value is prohibited and another sensor is used. Thus, detection of an appropriate value by sensor system 100 is guaranteed until all sensors become inoperable. Therefore, for that period, the user does not have to monitor individual sensors for failure due to deterioration thereof or to input an instruction for switching from the sensor that has failed to another sensor. In other words, sensor system 100 freer from maintenance of the sensor can be provided.

Sensor system 100 according to the second embodiment is suitable for use in a scene where the concentration of gas to be detected is stable when a device or an environment where the sensor system is provided is normal whereas the concentration of gas greatly fluctuates in a short period when the device or the environment is abnormal. In other words, the sensor system is effective in the scene where the detection value from the sensor is stable under a normal condition but the detection value greatly fluctuates under an abnormal condition. In such a scene, on the occurrence of abnormality, the detection value from the sensor abruptly greatly fluctuates and hence the abnormality can be detected, whereas when the detection value relatively gently and slightly fluctuates due to deterioration of the sensor under the normal condition, deterioration thereof can be detected. Alternatively, allowing for occurrence of sudden failure of the sensor under the normal condition, when the detection value therefrom abruptly fluctuates, the detection value from the next sensor may promptly be referred to, and when the detection value is within a normal range, determination as sudden failure of the sensor rather than abnormality of the device or the environment may be made.

In view of possibility of such sudden failure of the sensor, in the second embodiment, the sensors are used by rotation each for second period T2 shorter than first period T1 in the first embodiment. Then, if a sensor suddenly fails, the sudden failure can more quickly be noticed and another sensor can be used. The sudden failure is assumed to encompass also unexpected abrupt deterioration of the sensor.

3-3. Third Embodiment

In a third embodiment, such control that a plurality of sensors can be monitored for failure by using the sensors in pairs will now be described.

Figure 7:
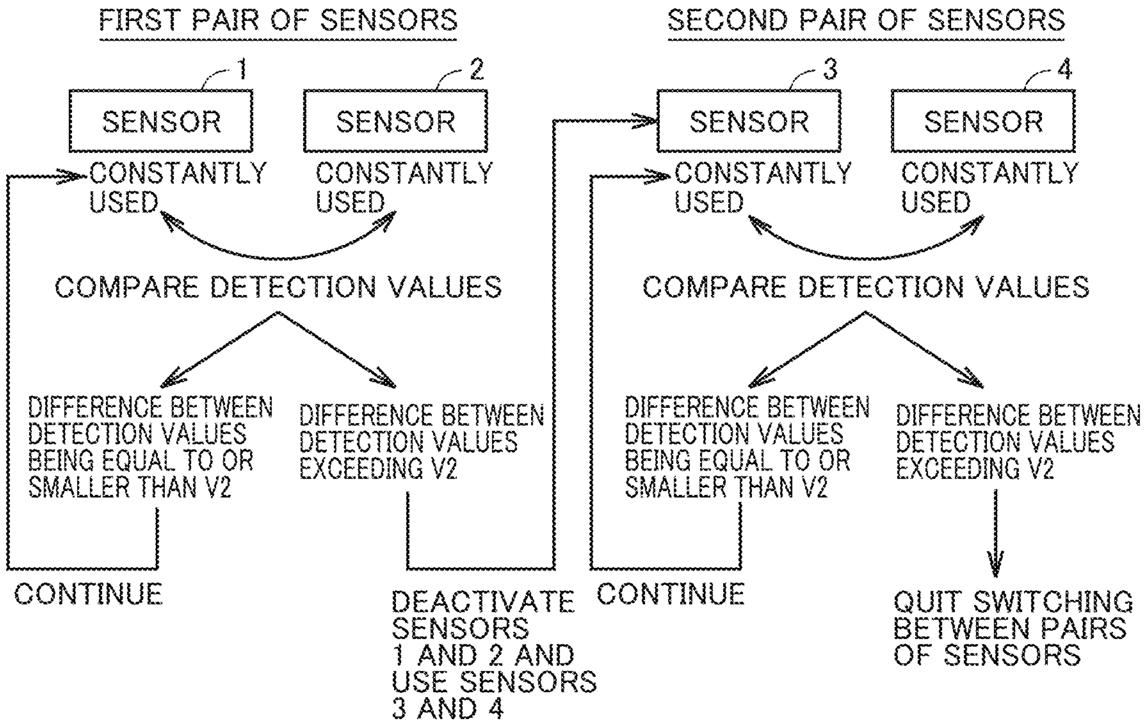
FIG. 7 is a schematic diagram for illustrating control in the sensor system according to a third embodiment.

FIG. 7 is a schematic diagram for illustrating control in sensor system 100 according to the third embodiment. FIG. 7 illustrates an example in which four sensors are provided and two pairs of sensors are provided. Referring to FIG. 7, initially, sensors 1 and 2 are used as a first pair of sensors. While the first pair of sensors is used, both of sensor 1 and sensor 2 are constantly driven. A detection value from sensor 1 and a detection value from sensor 2 are compared with each other, and when a difference therebetween is equal to or smaller than a second threshold value V2, use of this pair of sensors is continued. Second threshold value V2 is, for example, equal to first threshold value V1. When the difference between the detection value from sensor 1 and the detection value from sensor 2 exceeds second threshold value V2, on the other hand, the first pair of sensors is deactivated and a second pair of sensors consisting of sensors 3 and 4 is used. In the second pair of sensors as well, as in the first pair of sensors, a detection value from sensor 3 and a detection value from sensor 4 are compared with each other, and when a difference therebetween is equal to or smaller than second threshold value V2, use of this pair of sensors is continued. On the other hand, when the difference between the detection value from sensor 3 and the detection value from sensor 4 exceeds second threshold value V2 and when there is an unused pair of sensors in sensor system 100, switching to a new pair of sensors is made. So long as there is such a new pair of sensors, switching among pairs of sensors is continued. When sensors 3 and 4 are the last pair of sensors as in the example in FIG. 7, however, switching between the pairs of sensors ends. In other words, in sensor system 100 according to the third embodiment, the prescribed condition is a "condition that the difference in detection value between the sensors included in the pair of sensors exceeds second threshold value V2" and switching between/among the pair of sensors is made in accordance with the condition. The condition above corresponds to one example of the "third condition" in the present disclosure.

Figure 8:
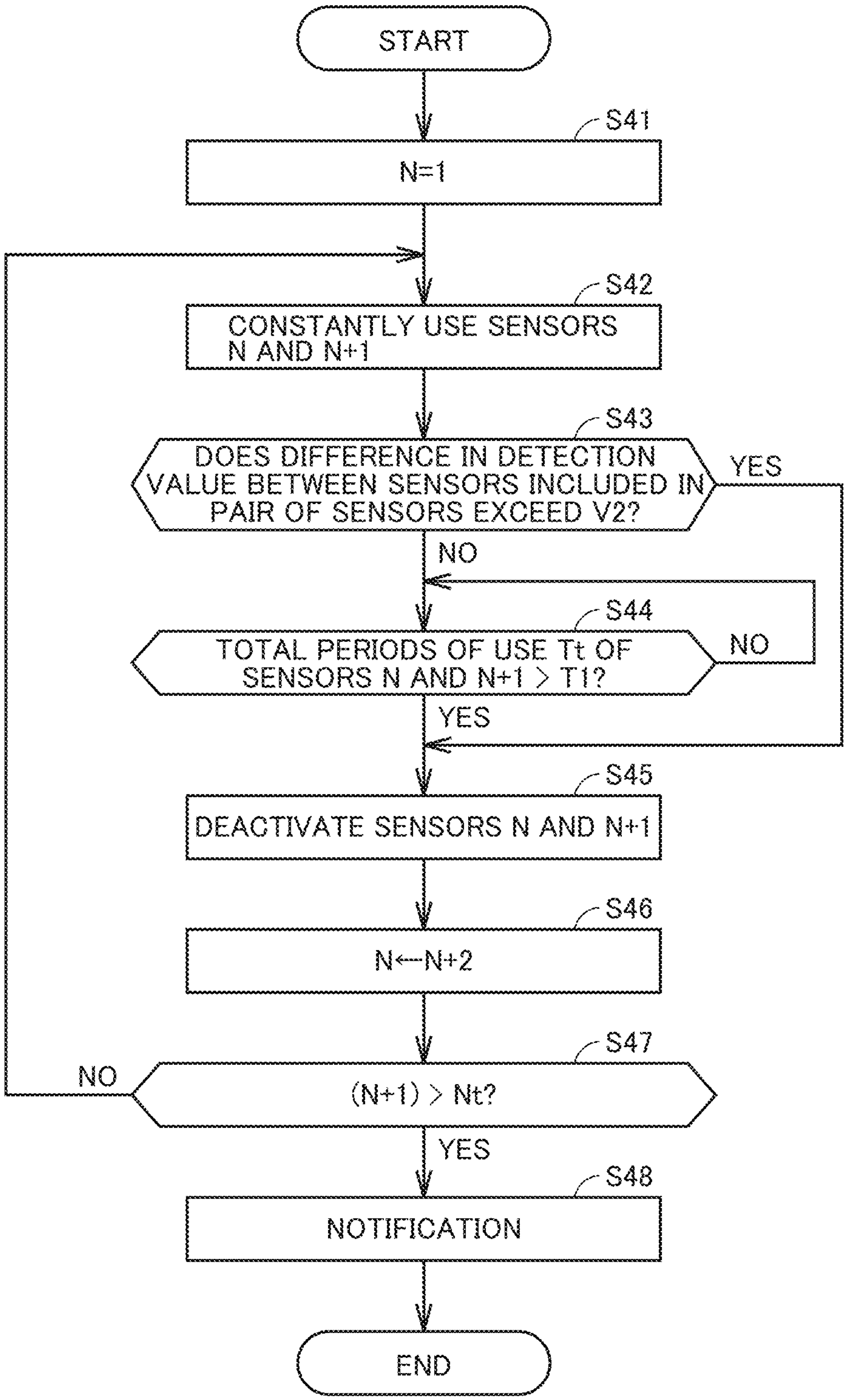
FIG. 8 is a flowchart showing control processing in the sensor system according to the third embodiment.

FIG. 8 is a flowchart showing control processing in sensor system 100 according to the third embodiment. Processing in FIG. 8 is performed by sensor system 100 including controller 10.

In S41, controller 10 substitutes 1 into counter N.

In S42, controller 10 causes use of sensors N and N+1 as the pair of sensors.

In S43, controller 10 determines whether or not the difference in detection value between the sensors included in the pair of sensors being used exceeds second threshold value V2.

When the difference in detection value between the sensors included in the pair of sensors being used is equal to or smaller than second threshold value V2 (NO in S43), in S44, controller 10 determines whether or not total periods of use Tt of sensors N and N+1 exceed first period T1.

When the difference in detection value between the sensors included in the pair of sensors being used exceeds second threshold value V2 (YES in S43) or when total periods of use Tt exceed first period T1 (YES in S44), in S45, controller 10 deactivates sensors N and N+1.

In S46, controller 10 increments the value of counter N by two.

In S47, controller 10 determines whether or not (N+1) exceeds defined value Nt.

When (N+1) is equal to or smaller than defined value Nt (NO in S47), controller 10 has the process return to S42.

When (N+1) exceeds defined value Nt (YES in S47), controller 10 quits the process relating to switching between/among the sensors. Before quitting the process, however, in S48, controller 10 may have notification unit 15 to give notification that the detection value from at least one of the last pair of sensors is inappropriate. Controller 10 can thus remind the user of replacement of the sensor in sensor system 100 or replacement of sensor system 100 itself. At this time, as temporary measures before replacement of the sensor, controller 10 may be configured such that only a sensor a detection value of which is estimated as being appropriate is used. An exemplary sensor the detection value of which is estimated as being appropriate is a sensor that gives a detection value within a range assumed as being reasonable based on the environment of use. Another exemplary sensor is a sensor that gives a larger detection value.

As set forth above, in control processing in sensor system 100 according to the third embodiment, when the difference between detection values from the sensors included in the pair of sensors (corresponding to the "first pair of sensors") being used exceeds second threshold value V2, controller 10 makes switching from the pair of sensors being used to the next pair of sensors (corresponding to the "second pair of sensors"). Thus, a period for which the sensor system can be used without maintenance of the sensor can be longer as in the first embodiment. In the sensor system according to the third embodiment, the difference in detection value between the sensors included in the pair of sensors is always compared, so that whether variation in detection value from the sensor represents variation in concentration of gas to be detected or originates from failure of the sensor can be determined simultaneously with detection of variation in detection value. Therefore, even in an environment where fluctuation of the concentration of gas is likely even under the normal condition, failure of the sensor can immediately be detected and the next sensor can be used. Therefore, the user does not have to pay attention to failure of individual sensors, and while at least one pair of sensors appropriately operates, use of sensor system 100 can be continued. In other words, in a scene broader than in the second embodiment, sensor system 100 freer from maintenance of the sensor than in the first embodiment can be provided.

3-4. Fourth Embodiment

In a fourth embodiment, such control that a sensor for monitoring the detection value from the sensor is provided as in the third embodiment and deterioration of the sensor involved with monitoring can further be suppressed by decreasing a time period of use of the sensor for monitoring will now be described.

Figure 9:
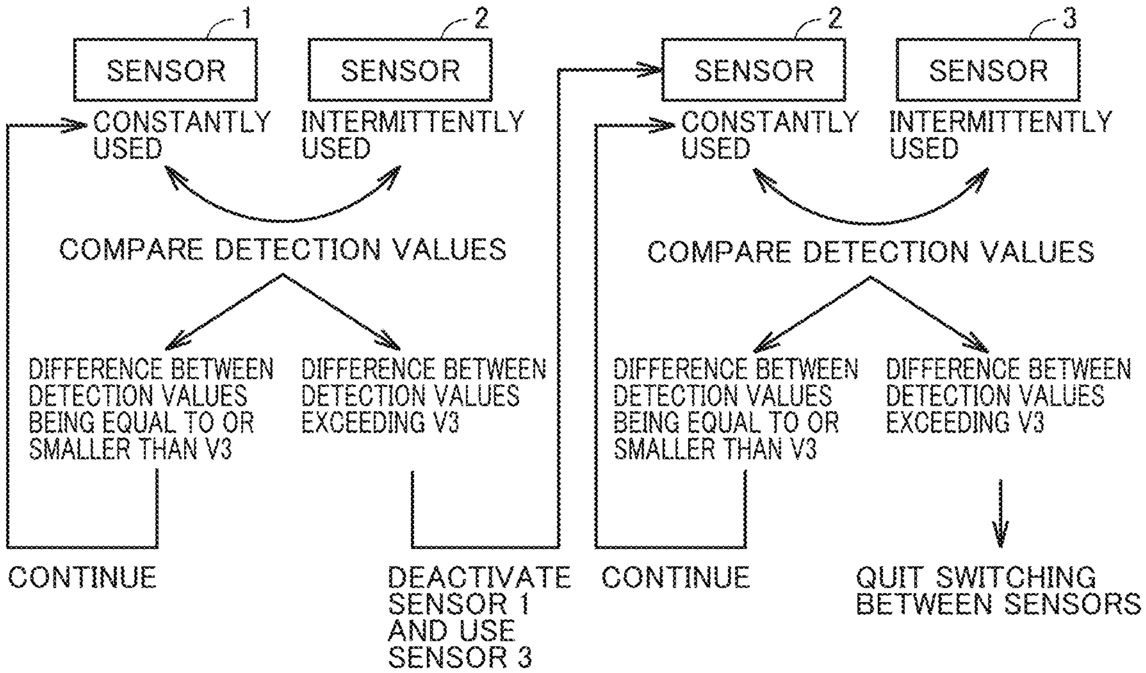
FIG. 9 is a schematic diagram for illustrating control in the sensor system according to a fourth embodiment.

FIG. 9 is a schematic diagram for illustrating control in sensor system 100 according to the fourth embodiment. FIG. 9 illustrates an example where there are three sensors. Referring to FIG. 9, initially, sensors 1 and 2 are used. Sensor 1 is constantly used and sensor 2 is intermittently used. Sensor 2 is used, for example, for several minutes a day. In another example of sensor 2, sensor 2 may be used for one second in a few minutes. When a difference between detection values from sensors 1 and 2 is equal to or smaller than a third threshold value V3 while sensors 1 and 2 are being used, use of sensors 1 and 2 is continued. Third threshold value V3 is, for example, equal to first threshold value V1. When the difference between the detection values from sensors 1 and 2 exceeds third threshold value V3, on the other hand, the sensor estimated as having deteriorated is deactivated. In the example in FIG. 9, since sensor 1 that is constantly used and longer in total period of use is estimated as having deteriorated, sensor 1 is deactivated and sensor 3 is newly used. Sensor 2 that has already been used is now constantly used, and sensor 3 is intermittently used. Use of sensors 2 and 3 is also continued similarly to sensors 1 and 2 while the difference in detection value between the sensors is equal to or smaller than third threshold value V3. On the other hand, when the difference between the detection values from sensors 2 and 3 exceeds third threshold value V3 and when there is an unused sensor in sensor system 100, switching to the new sensor is made. Specifically, sensor 3 is now constantly used and the new sensor is intermittently used. So long as there is a new sensor as such, switching among the sensors is continued. When sensor 3 is the last sensor as in the example in FIG. 9, however, switching among the sensors ends. In other words, in sensor system 100 according to the fourth embodiment, the prescribed condition is a "condition that the difference in detection value between two sensors being used exceeds the third threshold value" and switching among the sensors is made in accordance with the condition. The condition above corresponds to one example of the "fourth condition" in the present disclosure.

Figure 10:
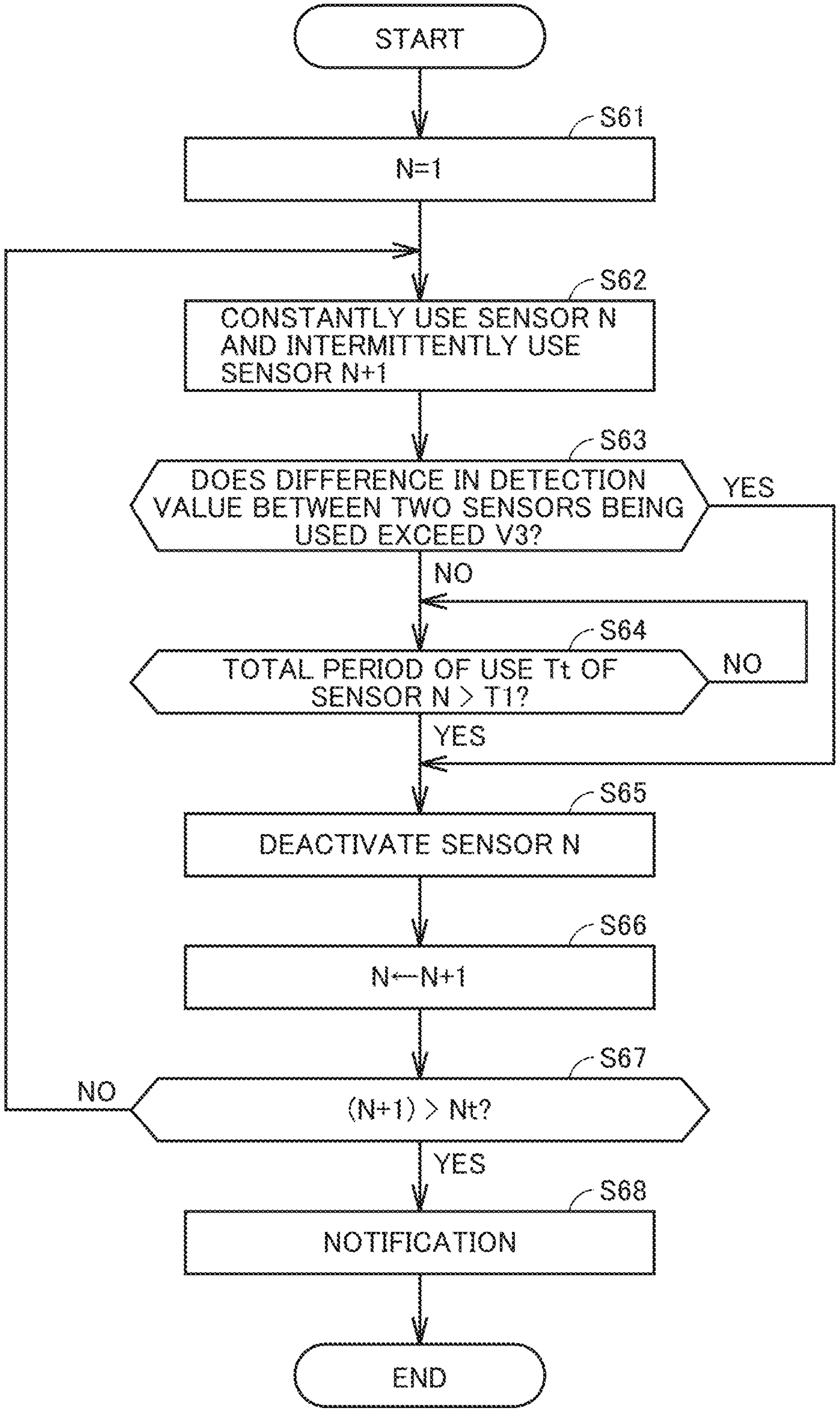
FIG. 10 is a flowchart showing control processing in the sensor system according to the fourth embodiment.

FIG. 10 is a flowchart showing control processing in sensor system 100 according to the fourth embodiment. Processing in FIG. 10 is performed by sensor system 100 including controller 10.

In S61, controller 10 substitutes 1 into counter N.

In S62, controller 10 causes sensor N to constantly be used and causes sensor (N+1) to intermittently be used.

In S63, controller 10 determines whether or not the difference in detection value between the two sensors being used exceeds third threshold value V3.

When the difference in detection value between the two sensors being used is equal to or smaller than third threshold value V3 (NO in S63), in S64, controller 10 determines whether or not a total period of use Tt of sensor N exceeds first period T1.

When the difference in detection value between the two sensors being used exceeds third threshold value V3 (YES in S63) or when total period of use Tt exceeds first period T1 (YES in S64), in S65, controller 10 deactivates sensor N.

In S66, controller 10 increments the value of counter N by one.

In S67, controller 10 determines whether or not (N+1) exceeds defined value Nt.

When (N+1) is equal to or smaller than defined value Nt (NO in S67), controller 10 has the process return to S62.

When (N+1) exceeds defined value Nt (YES in S67), controller 10 quits the process relating to switching among the sensors. Before quitting the process, however, in S68, controller 10 may have notification unit 15 to give notification that at least one of the last two sensors has failed. Controller 10 can thus remind the user of replacement of the sensor in sensor system 100 or replacement of sensor system 100 itself. At this time, as temporary measures before replacement of the sensor, controller 10 may be configured such that only a sensor a detection value of which is estimated as being appropriate is used. An exemplary sensor the detection value of which is estimated as being appropriate is a sensor shorter in total period of use Tt (sensor 3 in the example in FIG. 9). Another exemplary sensor is a sensor that gives a larger detection value within a range of detection values assumed as being reasonable based on the environment of use.

Though sensor 1 longer in total period of use Tt is estimated as having deteriorated and deactivated in S63 and S65, processing for estimating and deactivating the sensor that has failed is not limited to the example above. For example, while intermittent use of sensor 2 is continued, switching to the sensor to constantly be used may sequentially be made. Alternatively, for example, a sensor that gives a detection value that clearly seems to be inappropriate in view of circumstances may be determined as having failed and deactivated. For example, a sensor that gives a smaller detection value within a range of detection values that seems to be reasonable under the circumstances may be determined as having deteriorated and deactivated.

As set forth above, in control processing in sensor system 100 according to the fourth embodiment, when the difference in detection value between two sensors being used while controller 10 causes one sensor (corresponding to the "third sensor") to constantly be used and causes the other sensor (corresponding to the "fourth sensor") to intermittently be used, the controller deactivates the sensor that has constantly been used and makes switching such that the sensor that has intermittently been used is constantly used and causes a new sensor (corresponding to the "fifth sensor") to intermittently be used. Thus, a period for which the sensor system can be used without maintenance of the sensor can be longer as in the first embodiment. Substantially similarly to the sensor system according to the third embodiment, while the sensors are monitored for failure by comparison of the detection values from the two sensors, the sensor involved with monitoring can be used for a longer period by decreasing the total time of use of the sensor involved with monitoring. Therefore, a period for which the sensor system is kept operable without maintenance of the sensor can further be longer than in the third embodiment.

The embodiments above can be combined within the consistent scope.

In the embodiments above, the sensor "being constantly used" encompasses an example where the sensor is continuously used only while detection of the concentration of gas is required and is deactivated when detection is not required. For example, in measurement of the concentration of gas in a room with sensor system 100, continuous use of the sensor only while the room is used is also encompassed in "being constantly used." A duration and a frequency of continuous use are set as appropriate in an application. Similarly, a duration and a frequency of "intermittent use" of the sensor are also set as appropriate in an application.

4. Application

Sensor system 100 according to the embodiments above can be used in applications below.

4-1. Application to Small-Sized Oxygen Sensor of Portable Information Terminal Sensor system 100 according to the embodiments is incorporated as a small-sized oxygen sensor system, in a mobile (portable information terminal) such as a smartwatch or a smartphone. The user can thus be notified of oxygen depletion in a small closed space into which the mobile is brought.

In a more specific example, when oxygen is depleted in a tent due to use of a lantern in the tent, alarm of the mobile can be generated. Depletion of oxygen refers, for example, to the concentration of oxygen becoming 18% or lower.

In the specific example, in particular, control for comparison of the difference in detection value between the sensors by simultaneous use of two or more sensors as in the third and fourth embodiments is effective. Thus, an oxygen depletion accident in a sensor system where only a single sensor is used at a time, due to erroneous detection of the oxygen concentration caused by failure of the sensor, can be prevented.

In the present specific example, abrupt (for example, in a unit of several seconds) lowering in concentration of oxygen is less likely, and the sensor should only be used in such an intermittent manner as being used once for one second in thirty seconds. Deterioration of the sensor can thus be suppressed and used for a long period. For example, when lifetime (corresponding to the "first period") of the sensor that is constantly used is 3000 hours, lifetime thereof in the case of intermittent use for one second in thirty seconds is 90,000 hours, which is thirty times longer than the former, and maintenance of the sensor is not necessary for more than ten years. Power consumption by the sensor is also suppressed. For example, in an example where electricity usage by the sensor that is constantly used is 30 mW, average power consumption in intermittent use for one second in thirty seconds is suppressed to 1 mW, which is one thirtieth of the former.

(4-2. Application to Monitoring of Oxygen Concentration in Industrial Application)

Sensor system 100 according to the present embodiment is applied to a sensor system that monitors the oxygen concentration in a place that may hermetically be sealed (an elevator, underground, or the like) or a place where oxygen may be depleted (a laboratory, a food storage, a desiccator, or the like). In addition, sensor system 100 according to the present embodiment is applied to a portable sensor system carried by a person (a worker or the like in a manhole or an underground construction site) who goes to a place where oxygen may be depleted.

A general commercially available galvanic cell sensor should be replaced in two years of use at 20° C. or in one year of use at 40° C.

In sensor system 100 according to the present embodiment, on the other hand, five pairs of sensors each having lifetime of approximately one year are incorporated so that a frequency of replacement of the sensors can be suppressed to five years. Cost for maintenance of the sensors can thus be reduced, and furthermore, reliability of the sensor system based on automatic guarantee against failure of the sensors is improved.

Specifically, in the first one year, one pair of sensors is used. When the difference between detection values from the two sensors included in the pair of sensors becomes large, determination as failure of any one sensor is made and switching to the second pair of sensors is made. Similarly, the third to fifth pairs of sensors can also be used. Continued use for approximately five years without maintenance of the sensors is allowed and cost for maintenance can be reduced.

4-3. Application to Portable Oxygen Inhaler

In general, for use of an oxygen inhaler while moving, a method of carrying an oxygen cylinder is adopted. A general oxygen cylinder is limited in its capacity of oxygen, and use thereof is limited to use for a short time period. Therefore, a small-sized portable oxygen inhaler is promising. The portable oxygen inhaler should incorporate an oxygen sensor system for detection of failure of an oxygen compressor, so as to monitor whether or not air at a high oxygen concentration can be supplied. Incorporation of a commercially available galvanic cell oxygen sensor gives rise to such a problem that an environment of use at 40° C. or higher is not covered by warranty.

When sensor system 100 according to the present embodiment is applied, on the other hand, unlike the galvanic cell oxygen sensor, the YSZ sensor including an oxygen concentration detector which reaches a high temperature of 500° C. is used, and hence the sensor system can be used also in a high-temperature area at 40° C. or higher.

In particular, by simultaneously using a plurality of sensors such as five sensors, even when a sensor suddenly fails, another sensor can be used. Therefore, possibility of adverse influence on a human body due to failure of a single sensor in an example where the single sensor is used can be eliminated.

In addition, by using the YSZ sensor as a humidity sensor, inspired oxygen can also moderately be humidified and the throat of a patient can also be prevented from drying.

4-4. Application to Fuel Cell

A fuel cell generates electric power by feed of air to an air electrode thereof. Dry air, however, causes lower efficiency in power generation or deterioration of the fuel cell. Therefore, air should sufficiently be humidified and then fed to the air electrode.

In general, there is no humidity sensor that is resistant to a high temperature and a high humidity (for example, a temperature equal to or higher than 90° C. and a relative humidity equal to or higher than 90%). Therefore, such measures as excessive humidification of air are taken for a general fuel cell. When condensation then occurs as a result of excessive humidification, resultant water is drained to overcome water flooding in the cell.

Humidification of air, however, consumes electric power. Therefore, improvement in efficiency of a fuel cell by suppression of excessive humidification to necessary and sufficient humidification to reduce electric power has been demanded.

Not the relative humidity but an absolute humidity is important for higher efficiency of the fuel cell. A well-known polymer humidity sensor measures the relative humidity. A YSZ cell included in present sensor system 100, on the other hand, can measure the absolute humidity rather than the relative humidity. Therefore, the water vapor concentration in air that is being supplied can directly be measured, without the temperature being measured.

The high temperature and the high humidity are an environment severe to the sensor. By including a plurality of sensors as in sensor system 100 according to the present embodiment and using another sensor when a single sensor fails, measurement of the water vapor concentration can be continued even in the severe environment.

It should be understood that the embodiments disclosed herein are illustrative and non-restrictive in every respect. The scope of the present invention is defined by the terms of the claims rather than the description above and is intended to include any modifications within the scope and meaning equivalent to the terms of the claims.

REFERENCE SIGNS LIST

1, 2, 3, 4, N, X, Y sensor; 10 controller; 11 processor; 12 memory; 13 communication unit; 14 input unit; 15 notification unit; 20 drive device; 100 sensor system; SW switch; T1 first period; T2 second period; Te period of continuous use; Tt total period of use; V1 first threshold value; V2 second threshold value; V3 third threshold value.

The invention claimed is:

1. A sensor system comprising:
- a plurality of yttria-stabilized zirconia sensors that are driven by a driver; and
- a controller configured to control the driver, wherein
- the controller is configured to sequentially switch between/among the plurality of sensors based on a prescribed condition,
- the plurality of sensors include a first sensor, a second sensor, and a third sensor,
- the prescribed condition includes a first condition that a difference in detection value between two sensors being used exceeds a first threshold value, and
- the controller is configured to deactivate the first sensor, cause the second sensor to be used constantly, and cause the third sensor to be used intermittently when the first condition is satisfied while the first sensor is being used constantly and the second sensor is being used intermittently.

2. The sensor system according to claim 1, wherein the prescribed condition includes a second condition that a total period of use of each of the plurality of sensors exceeds a first period, and the controller is configured to cause switching from the first sensor to the second sensor when the second condition is satisfied during use of the first sensor.

3. The sensor system according to claim 1, wherein the prescribed condition includes a third condition that a period of continuous use of each of the plurality of sensors exceeds a second period, and the controller is configured to control the use of the plurality of sensors by switching among the plurality of sensors, based on the third condition.

4. The sensor system according to claim 3, wherein the controller is configured to prohibit use of a sensor being used when a difference between a detection value from the sensor being used and a detection value from at least one other sensor exceeds a second threshold value.

5. The sensor system according to claim 1, wherein the plurality of sensors include groupings of a first pair of sensors and a second pair of sensors, the prescribed condition includes a fourth condition that a difference in detection value between sensors included in a pair of sensors being used exceeds a third threshold value, and the controller is configured to cause switching from the first pair of sensors to the second pair of sensors when the fourth condition is satisfied while the first pair of sensor is being used.

6. The sensor system according to claim 1, wherein each of the plurality of sensors is adapted for high-temperature measurement of a concentration of at least one of oxygen and water vapor, and each of the plurality of sensors is susceptible to deterioration due to high-temperature conditions.

7. The sensor system according to claim 1, wherein each of the plurality of sensors is an yttria-stabilized zirconia sensor having a maximum dimension not larger than 5 mm.

8. The sensor system according to claim 7, wherein each of the plurality of sensors is an yttria-stabilized zirconia sensor having a maximum dimension not larger than 1 mm.

9. The sensor system according to claim 1, wherein the plurality of sensors include groupings of a first pair of sensors and a second pair of sensors, the prescribed condition includes a fourth condition that a difference in detection value between sensors included in a pair of sensors being used exceeds a third threshold value, and the controller is configured to cause switching from the first pair of sensors to the second pair of sensors when the fourth condition is satisfied while the first pair of sensor is being used.

10. A sensor system comprising:

a plurality of sensors that are driven by a driver; and a controller configured to control the driver, wherein the controller is configured to sequentially switch between/among the plurality of sensors based on a prescribed condition, the plurality of sensors include a first sensor, a second sensor, and a third sensor, the prescribed condition includes a first condition that a difference in detection value between two sensors being used exceeds a first threshold value, and the controller is configured to deactivate the first sensor, cause the second sensor to be used constantly, and cause the third sensor to be used intermittently when the first condition is satisfied while the first sensor is being used constantly and the second sensor is being used intermittently.

11. The sensor system according to claim 10, wherein the prescribed condition includes a second condition that a total period of use of each of the plurality of sensors exceeds a first period, and the controller is configured to cause switching from the first sensor to the second sensor when the second condition is satisfied during use of the first sensor.

12. The sensor system according to claim 10, wherein the prescribed condition includes a third condition that a period of continuous use of each of the plurality of sensors exceeds a second period, and the controller is configured to control the use of the plurality of sensors by switching among the plurality of sensors based on the third condition.

13. The sensor system according to claim 12, wherein the controller is configured to prohibit use of a sensor being used when a difference between a detection value from the sensor being used and a detection value from at least one other sensor exceeds a second threshold value.

14. The sensor system according to claim 10, wherein each of the plurality of sensors is adapted for high-temperature measurement of a concentration of at least one of oxygen and water vapor, and each of the plurality of sensors is susceptible to deterioration due to high-temperature conditions.

15. The sensor system according to claim 10, wherein each of the plurality of sensors has a maximum dimension not larger than 5 mm.

16. The sensor system according to claim 15, wherein each of the plurality of sensors has a maximum dimension not larger than 1 mm.

* * * * *